(12) United States Patent
Perez de Alejo Fortun et al.

(10) Patent No.: US 10,674,938 B2
(45) Date of Patent: Jun. 9, 2020

(54) APPARATUS AND METHOD FOR DETECTING HEALTH DETERIORATION

(71) Applicant: LINDE AKTIENGESELLSCHAFT, Munich (DE)

(72) Inventors: Rigoberto Perez de Alejo Fortun, Guildford (GB); Mercedes Franco Gay, Madrid (ES)

(73) Assignee: LINDE AKTIENGESELLSCHAFT, Munich (DE)

( * ) Notice: Subject to any disclaimer, the term of this patent is extended or adjusted under 35 U.S.C. 154(b) by 483 days.

(21) Appl. No.: 15/033,344

(22) PCT Filed: Oct. 3, 2014

(86) PCT No.: PCT/EP2014/071272
§ 371 (c)(1),
(2) Date: Apr. 29, 2016

(87) PCT Pub. No.: WO2015/062811
PCT Pub. Date: May 7, 2015

(65) Prior Publication Data
US 2016/0242675 A1 Aug. 25, 2016

(30) Foreign Application Priority Data

Nov. 1, 2013 (GB) .................................. 1319351.1

(51) Int. Cl.
*A61B 5/08* (2006.01)
*A61B 5/00* (2006.01)
(Continued)

(52) U.S. Cl.
CPC ............ *A61B 5/0816* (2013.01); *A61B 5/087* (2013.01); *A61B 5/4842* (2013.01);
(Continued)

(58) Field of Classification Search
CPC ....... A61B 5/0816; A61B 5/087; G01F 5/005; G01F 1/36; A61M 16/0858; A61M 2016/003
See application file for complete search history.

(56) References Cited

U.S. PATENT DOCUMENTS 4,096,746 A 6/1978 Wilson et al.
6,389,364 B1 * 5/2002 Vyers .................... G01F 1/6847
137/486

(Continued)

FOREIGN PATENT DOCUMENTS

EP 2147693 A1 1/2010
EP 2245985 A1 11/2010
(Continued)

OTHER PUBLICATIONS

Combined Search and Examination Report of the GB Intellectual Property Office from Application No. GB1319351.1, dated May 2, 2014, 6 pages.

(Continued)

*Primary Examiner* — Jacqueline Cheng
*Assistant Examiner* — Tho Q Tran
(74) *Attorney, Agent, or Firm* — Meunier Carlin & Curfman LLC

(57) ABSTRACT

There is provided an apparatus for detecting the deteriorating health of a patient receiving gas from a respiratory device. The apparatus comprises a sensor unit configured to monitor a flow rate or pressure of a gas that is flowing in a pipe that connects the respiratory device to a gas delivery device worn by the patient, and a processor configured to measure a respiratory rate of the patient based on variations in the flow rate or pressure of gas in the pipe and to implement a trend analysis of the measured respiratory rate. The processor is configured to generate a warning when it determines that there is an upward trend in the measured (Continued)

respiratory rate and that a magnitude of the trend exceeds a threshold.

27 Claims, 3 Drawing Sheets

(51) Int. Cl.
    *G01F 1/36*       (2006.01)
    *G01F 5/00*       (2006.01)
    *G16H 40/60*     (2018.01)
    *A61M 16/08*     (2006.01)
    *A61B 5/087*     (2006.01)
    *A61M 16/00*     (2006.01)
    *G16H 20/40*     (2018.01)
    *A61B 5/024*     (2006.01)

(52) U.S. Cl.
    CPC .......... *A61B 5/7242* (2013.01); *A61B 5/7275* (2013.01); *A61B 5/746* (2013.01); *A61M 16/0858* (2014.02); *G01F 1/36* (2013.01); *G01F 5/005* (2013.01); *G16H 20/40* (2018.01); *G16H 40/60* (2018.01); *A61B 5/024* (2013.01); *A61B 5/4848* (2013.01); *A61B 5/7217* (2013.01); *A61B 5/7239* (2013.01); *A61B 5/7278* (2013.01); *A61M 2016/003* (2013.01); *A61M 2016/0027* (2013.01); *A61M 2202/0208* (2013.01); *A61M 2205/0216* (2013.01); *A61M 2230/42* (2013.01)

(56) References Cited

U.S. PATENT DOCUMENTS

| | | | |
|---|---|---|---|
| 2002/0174729 A1* | 11/2002 | Danninger | G01F 1/363 73/861.63 |
| 2003/0028221 A1* | 2/2003 | Zhu | A61N 1/3627 607/9 |
| 2004/0015337 A1* | 1/2004 | Thomas | G16H 50/20 703/11 |
| 2009/0234240 A1 | 9/2009 | Kuenzler et al. | |
| 2011/0009753 A1* | 1/2011 | Zhang | A61B 5/0205 600/484 |
| 2011/0213271 A1* | 9/2011 | Telfort | A61B 7/003 600/586 |
| 2011/0247703 A1 | 10/2011 | Brown | |
| 2012/0203128 A1 | 8/2012 | Levison et al. | |
| 2012/0271372 A1 | 10/2012 | Osorio | |
| 2012/0310051 A1* | 12/2012 | Addison | A61B 5/1455 600/301 |

FOREIGN PATENT DOCUMENTS

| | | |
|---|---|---|
| GB | 2440466 A | 1/2008 |
| WO | 2004/049912 A2 | 6/2004 |
| WO | 2005/074361 A2 | 8/2005 |

OTHER PUBLICATIONS

International Search Report and Written Opinion of the International Searching Authority from Application No. PCT/EP2014/071272, dated Mar. 17, 2015, 20 pages.
International Preliminary Report on Patentability of the International Preliminary Examining Authority from Application No. PCT/EP2014/071272, dated Oct. 20, 2015, 30 pages.

* cited by examiner

APPARATUS AND METHOD FOR DETECTING HEALTH DETERIORATION

The present invention relates to a method and apparatus for detecting deterioration in the health of an individual. In particular, the present invention provides an apparatus and method for detecting the deterioration in the health of a patient receiving gas from a respiratory device.

Domiciliary oxygen therapy refers to the provision of oxygen therapy at home for patients with hypoxaemia, which is subnormal oxygenation of arterial blood. Hypoxaemia may be due to a number of chronic, mainly respiratory, conditions, such as Chronic Obstructive Pulmonary Disease (COPD). Long-term oxygen therapy (LTOT) for the treatment of chronic hypoxaemia usually prescribes that oxygen (e.g. from an oxygen cylinder and/or oxygen concentrator machine) is used for a minimum of 15 hours a day.

A large proportion of the patients receiving LTOT will at some point experience a worsening in their condition that will eventually require admission to hospital for further treatment. This exacerbation of a patient's condition not only impacts on the health and quality of life of the patient's, but is also particularly expensive for healthcare providers as most patients do not seek treatment until there has been a significant worsening of their condition that then requires admission to and a stay in hospital for treatment. It would therefore be desirable to be able to automatically detect or predict when a patient's condition is becoming exacerbated, so that examination and treatment of the patient can be initiated promptly, before the condition worsens to the point that hospital admission is a necessity.

WO2005/074361 proposes a method for predicting the onset of a clinical episode in which a pressure gauge is placed under a mattress upon which a subject sleeps to monitor the body motion of the subject during sleep. Some form of pattern analysis is then used to eliminate non-breathing related motion from the signal generated by the pressure gauge, and to extract breathing rate patterns from the remaining breathing-related motion, wherein the extracted breathing rate patterns include one or more of a slow trend breathing rate pattern, a breathing rate variability pattern, a breathing duty-cycle pattern, and interruptions in a breathing pattern. Comparison of the extracted breathing rate patterns to respective baseline patterns is then used to determine the onset of an attack.

Therefore, according to a first aspect there is provided an apparatus for detecting the deteriorating health of a patient receiving gas from a respiratory device. The apparatus comprises a sensor unit configured to monitor a flow rate or pressure of a gas that is flowing in a pipe that connects the respiratory device to a gas delivery device worn by the patient, and a processor configured to measure a respiratory rate of the patient based on variations in the flow rate or pressure of gas in the pipe and to implement a trend analysis of the measured respiratory rate. The processor is configured to generate a warning when it determines that there is an upward trend in the measured respiratory rate and that a magnitude of the trend exceeds a threshold.

The sensor unit comprises a sensor device configured to monitor the variations in the flow rate or pressure that are induced by the respiration of the patient and to output a signal that is proportional to a derivative of the flow rate or pressure with respect to time. The processor is configured to detect peaks in the monitored flow rate or pressure by implementing discrete-time integration of the output of the sensor device and to determine a measure of the respiratory rate of the patient using the separation between the detected peaks, to determine the flow rate or pressure of a flow that is induced by the respiration of the patient, and to then process the determined flow rate or pressure to detect local maxima.

The sensor device may comprise a differential pressure sensor having first and second pneumatic input ports, the first pneumatic input port being configured to receive a flow of gas from a first point in the pipe and the second pneumatic input port being configured to receive a flow of gas from a second point in the pipe, wherein the second pneumatic input port is also configured to delay the flow of gas that flows from the pipe to the differential pressure sensor.

The second pneumatic input port may comprise a porous material within a hollow centre of the second pneumatic input port. Alternatively, at least a portion of the second pneumatic input port may be formed from a resilient material.

The processor may be configured to use one or both of a threshold peak width and a threshold peak amplitude to exclude noise when measuring the respiratory rate of the patient.

The sensor unit may be configured to implement sampling phases at predefined intervals when variations in the flow rate or pressure are detected, and the flow rate or pressure is monitored for the duration of each sampling phase. The processor may then be configured to calculate a median value for the separation between the peaks detected during each sampling phase and to use the median value as a measure of the respiratory rate of the patient.

The processor may be configured to implement the trend analysis at the end of each of a plurality of daily time slots using the respiratory rate measured during the latest time slot and corresponding time slots of preceding days.

The processor may be configured to implement a trend analysis that comprises calculating a C-statistic for the measured respiratory rate. The processor may then be configured to generate a warning when the calculated C-statistic indicates a trend and a comparison of the measured respiratory rate with a characteristic respiratory rate indicates an upward trend. The processor may be configured to determine a characteristic respiratory rate by averaging the respiratory rate measured over a reference period of at least a predefined number of days.

The processor may be configured to implement the trend analysis using the respiratory rate measured over an analysis period of a predefined number of days. The processor may be configured to determine the characteristic respiratory rate by averaging the respiratory rate measured over the days preceding the analysis period.

The apparatus may be configured to be used with a domiciliary respiratory device. The apparatus may further comprise a transceiver configured to communicate with a remote computer device. The processor may then be configured to cause a communication to be sent using the transceiver that warns a remote compute device that the patient's health is likely to be deteriorating.

The apparatus may be configured to be used with a respiratory device that is an oxygen supply device and to monitor a flow rate or pressure of oxygen provided by the oxygen supply device. Alternatively, the apparatus may be configured to be used with a respiratory device that is a ventilator and to monitor a flow rate or pressure of air provided by the ventilator.

According to a second aspect there is provided a method of detecting exacerbation of a medical condition of a patient receiving gas from a respiratory device. The method comprises using a sensor unit to monitor a flow rate or pressure of a gas that is flowing in a pipe that connects the respiratory device to a gas delivery device worn by the patient, using a processor to measure a respiratory rate of the patient based on variations in the flow rate or pressure of gas in the pipe, and using the processor to implement a trend analysis of the measured respiratory rate. The method further comprises, when the processor determines that there is an upward trend in the measured respiratory rate and that a magnitude of the trend exceeds a threshold, generating a warning.

The step of using a sensor unit to monitor a flow rate or pressure of a gas that is flowing in a pipe that connects the respiratory device to a gas delivery device worn by the patient comprises using a sensor device of the sensor unit to monitor the variations in the flow rate or pressure that are induced by the respiration of the patient and to output a signal that is proportional to a derivative of the flow rate or pressure with respect to time.

The step of using a processor to measure a respiratory rate of the patient based on variations in the flow rate or pressure of gas in the pipe comprises detecting peaks in the monitored flow rate or pressure by implementing discrete-time integration of the output of the sensor device, and determining a measure of the respiratory rate of the patient using the separation between the detected peaks to determine the flow rate or pressure of a flow that is induced by the respiration of the patient, and then processing the determined flow rate or pressure to detect local maxima.

The step of detecting peaks in the monitored flow rate or pressure may comprise using one or both of a threshold peak width and a threshold peak amplitude to exclude noise when measuring the respiratory rate of the patient.

The method may comprise implementing sampling phases at predefined intervals when variations in the flow rate or pressure are detected, and monitoring the flow rate or pressure for the duration of each sampling phase. The method may then comprise calculating a median value for the separation between the peaks detected during each sampling phase, and using the median value as a measure of the respiratory rate of the patient.

The step of using the processor to implement a trend analysis of the measured respiratory rate may comprise implementing the trend analysis at the end of each of a plurality of daily time slots using the respiratory rate measured during the latest time slot and corresponding time slots of preceding days.

The step of using the processor to implement a trend analysis of the measured respiratory rate may comprise calculating a C-statistic for the measured respiratory rate. The method may then further comprise generating a warning when the calculated C-statistic indicates a trend and a comparison of the measured respiratory rate with a characteristic respiratory rate indicates an upward trend.

The method may further comprise determining a characteristic respiratory rate by averaging the respiratory rate measured over a reference period of at least a predefined number of days. The step of using the processor to implement a trend analysis of the measured respiratory rate may comprise using the respiratory rate measured over an analysis period of a predefined number of days. The step of determining a characteristic respiratory rate may then comprise averaging the respiratory rate measured over the days preceding the analysis period.

The present invention will now be more particularly described by way of example only with reference to the accompanying drawings, in which.

The present inventors have determined that, for patients receiving LTOT, there will typically be an increase in the respiratory rate (i.e. the number of breaths taken within a set amount of time) of a patient over a period of 4 to 5 days prior to the admission of the patient to hospital due to the exacerbation of their condition. This trend can therefore be used as a basis for detecting in advance when there is a high likelihood that a patient's condition is going to exacerbate to the extent that may require hospitalization. Being able to pre-empt the exacerbation of a patient's condition can allow action to be taken that will prevent the need for the patient to be admitted to hospital or, at the least, that will reduce the length of time that the patient will need to spend in hospital, thereby improving the health and well-being of the patient and reducing costs that arise from hospital admissions.

In addition, it is expected that for patients receiving other forms of respiratory therapy a similar trend would also be displayed when there is deterioration in their health, and that the automatic detection/prediction of the deteriorating health of a patient receiving any form of respiratory therapy would be advantageous. By way of example, continuous positive airway pressure (CPAP) is a treatment that uses a domiciliary respiratory device to provide a continuous positive flow of air to keep the airways of a patient open, and is typically a treatment for people who have breathing problems, such as sleep apnoea.

The present inventors have therefore developed a method for predicting/detecting the deteriorating health of a patient/subject receiving a supply of gas from a respiratory device that generally involves monitoring a gas in a line/pipe/hose that connects the respiratory device to a gas delivery device worn by the patient and thereby measuring the respiratory rate of the patient based on variations in the flow or pressure of gas in the pipe. A trend analysis of the measured respiratory rate can then be implemented and, when it is determined that there is an upward trend in the measured respiratory rate and that the magnitude of the trend exceeds a threshold, a warning can be generated that indicates that health of the patient is likely to be deteriorating.

Figure 1:
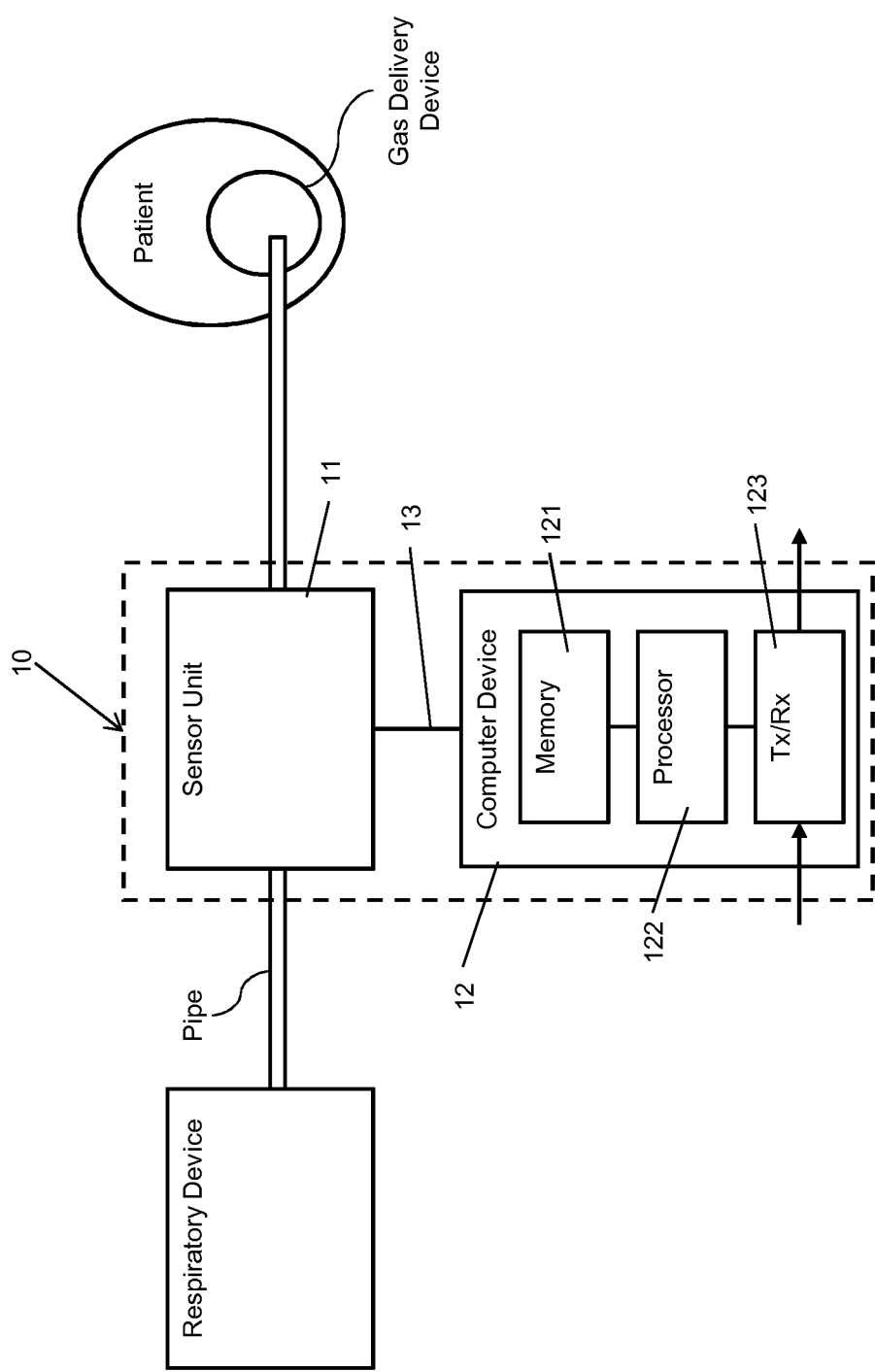
FIG. 1 illustrates schematically an embodiment of an apparatus for detecting exacerbation of a medical condition of a patient as described herein.

FIG. 1 illustrates schematically an example embodiment of an apparatus 10 suitable for predicting/detecting deterioration in the health of a patient receiving gas from a respiratory device.

The apparatus 10 comprises a sensor unit 11 and a computer device 12 connected to the sensor unit 11 via an interface 13. The computer device 12 comprises a memory 121, and a processor 122, and optionally a transmitter and a receiver 123. By way of example, the computer device 12 could be provided by a microcontroller, wherein a microcontroller is a computer device implemented on a single integrated circuit containing a processor core, memory, and programmable input/output peripherals.

The sensor unit 11 is configured to monitor the variation in the flow or pressure of a gas in a pipe that connects a respiratory device to a gas delivery device worn by the patient (e.g. a mask or cannula). The sensor unit 11 then provides the captured flow/pressure data to the computer device 12. The processor 122 provided as part of the computer device 12 is configured to measure the respiratory rate of the patient based on variations in the flow/pressure of gas in the pipe (i.e. using the data provided by the sensor unit 11), and to implement a trend analysis of the respiratory rate measured over a period of time. From this trend analysis, the processor 122 is configured to determine when there is an upward trend in the measured respiratory rate and compare the magnitude of this trend with a predefined threshold. When the processor 122 determines that the magnitude of the trend exceeds the threshold, the processor 122 is configured to generate a warning that the patient's health is likely to be deteriorating. By way of example, to generate a warning the processor 122 could be configured to activate a visual and/or audio warning signal using a visual indicator and/or speaker (not shown) provided as part of the apparatus 10. Alternatively, or in addition, the processor 122 could be configured to cause a communication to be sent using the transmitter 123 that informs a remote computer device or communication device (e.g. located at a hospital, doctor's office or other medical facility) that the patient's health is likely to be deteriorating.

Figure 2:
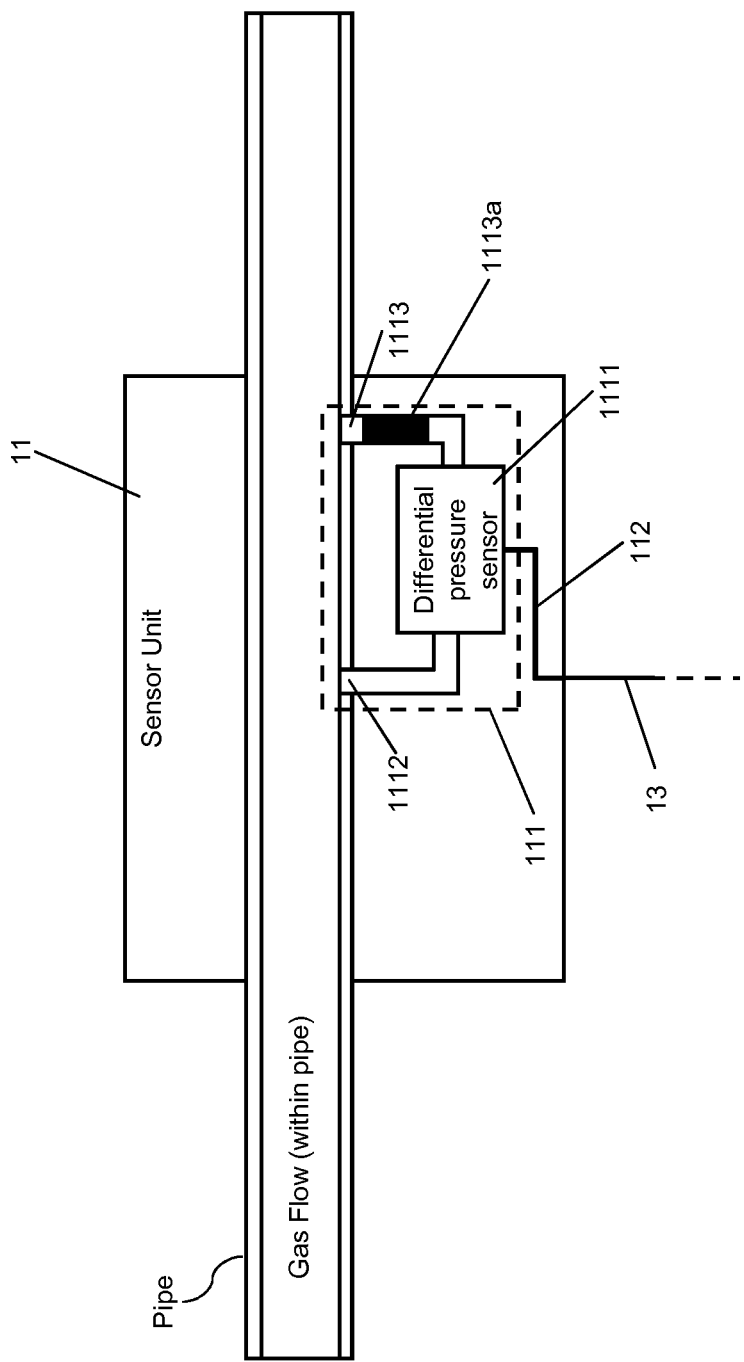
FIG. 2 illustrates schematically an embodiment of a sensor unit for use in the apparatus of FIG. 1.

FIG. 2 illustrates schematically an example embodiment of the sensor unit 11 of the apparatus 10 illustrated in FIG. 1. In this example, the sensor unit 11 comprises a sensor device 111 that is connected to or formed with the pipe and that has an output 112 to the interface 13 with the computer device 12.

In the example of FIG. 2, the sensor device 111 comprises a differential pressure sensor 1111 that has a first pneumatic input port 1112 and a second pneumatic input port 1113. The first pneumatic input port 1112 is configured to receive a flow of gas from a first point/location in the pipe and the second pneumatic input port 1113 is configured to receive a flow of gas from a second point/location in the pipe. The second pneumatic input port 1113 is also configured to delay the flow of gas that flows from the pipe to the differential pressure sensor. To do so, the second pneumatic input port 1113 includes a porous material 1113a (e.g. a sponge) within a hollow centre of the second pneumatic input port 1113. Alternatively, this delay in the flow could be achieved by forming at least a portion of the second pneumatic input port 1113 from an expandable, resilient material.

By inducing a delay in the flow of gas through the second pneumatic input port 1113 to the differential pressure sensor 1111, the differential pressure sensor 1111 effectively measures the variation in the pressure of the gas within the pipe, such that the signal generated/value measured by the differential pressure sensor 1111 is proportional to a derivative of the flow rate. In this regard, when the patient is using the respiratory device, there is a generally constant flow of gas in the pipe due to the pressure supplied by the respiratory device. The only significant source of variation in the flow/pressure of the gas in the pipe occurs due to the respiration (i.e. inhaling and exhaling) of the patient, wherein inhalation by the patient will increase the flow rate and exhalation will decrease the flow rate. By using a differential pressure sensor that is configured to output a signal that is proportional to a derivative of the flow rate, the sensor device 111 eliminates the effect of the constant flow/pressure of gas from the respiratory device that would otherwise saturate a conventional flowmeter and that would therefore limit the detection of relatively small variations due to the respiration of the patient. Consequently, the flow rate/pressure differential monitored by the sensor device 111 is limited to the variations that are induced by the respiration of the patient.

The flow/pressure data generated by the sensor device 111 can then be provided to the computer device 12 (i.e. using the interface 13) such that the processor 122 can measure the respiratory rate of the patient based on variations in the flow rate/pressure.

In an example embodiment, the processor 122 detects peaks in the monitored flow rate/pressure, and then determines a measure of the respiratory rate by calculating the separation between the peaks. In doing so, the processor 122 effectively determines the frequency of the variations in the flow rate/pressure, which will therefore provide an indication of the respiratory rate of the patient. To detect peaks in the monitored flow rate/pressure, the processor can be configured to implement discrete-time integration of the output of the sensor device 111 to determine the flow rate/pressure of the flow that is induced by the respiration of the patient, and to then process the monitored flow rate/pressure to detect local maxima. In an alternative configuration which is not an embodiment of the invention, the processor can be configured to detect a peak by determining when the output of the sensor device indicates that the derivative of the monitored flow rate/pressure is zero and to then determine if this relates to a local maxima.

The second pneumatic input port 1113 of the differential pressure sensor 1111 should be configured such that the delay induced in the flow of gas therethrough is in the order of, or higher than, the minimum respiratory frequency that is to be measured by the system. For example, this could be achieved by selecting a suitable porosity and length for a porous material 1113a used in the hollow centre of the second pneumatic input port 1113. Doing so ensures that the sensor device 111 acts as a high pass filter that will eliminate the constant flow/pressure (that has a frequency of zero) produced by the respiratory device and will pass the higher frequency variations produced by the respiration of the patient, such that the monitored flow rate/pressure is limited to the variations that are induced by the respiration of the patient.

Figure 3:
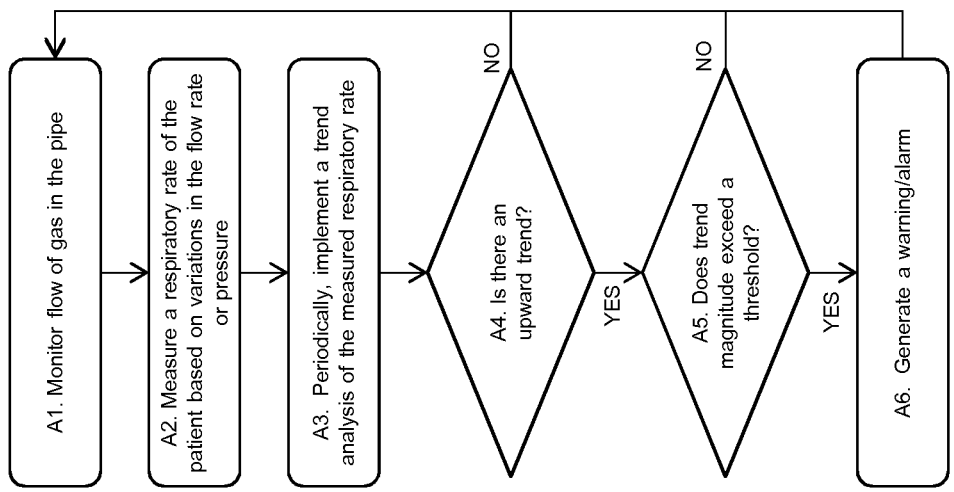
FIG. 3 is a flow diagram illustrating an embodiment of a method for detecting exacerbation of a medical condition as described herein.

FIG. 3 is a flow diagram illustrating an embodiment of a process for predicting/detecting deterioration in the health of a patient receiving gas from a respiratory device. The steps performed are as follows:

A1. The sensor unit 11 monitors a flow of gas in the pipe that connects the respiratory device to a gas delivery device worn by the patient. The sensor unit 11 then provides captured flow/pressure data to the computer device 12. For example, this flow data could comprise values that are proportional to a derivative of the flow rate/pressure.

A2. The processor 122 provided as part of the computer device 12 then measures the respiratory rate of the patient based on variations in the flow/pressure of the gas in the pipe. By way of example, the processor 122 could detect peaks in the monitored flow rate/pressure, and then determine a measure of the respiratory rate by calculating the separation between the peaks.

A3. Periodically, the processor 122 implements a trend analysis of the respiratory rate measured over a period time. Typically, the processor 122 would be configured to implement a trend analysis of the respiratory rate measured over an analysis period of a predefined number of days.

A4. The processor 122 then determines if the trend analysis indicates an upward trend in the measured respiratory rate. If the processor determines that there is an upward trend in the measured respiratory rate, then the process proceeds to step A5. If the processor determines that there is not an upward trend in the measured respiratory rate, then the process returns to step A1.

A5. If the processor 122 determines that there is an upward trend in the measured respiratory rate, the processor 122 then determines if the magnitude of the trend exceeds a predefined threshold. If the processor 122 determines that the magnitude of the upward trend does exceed the threshold, then the process proceeds to step A6. If the processor determines that the trend does not exceed the threshold, then the process returns to step A1.

A6. If the processor 122 determines that the magnitude of the upward trend does exceed the threshold, then the processor 122 causes the generation of a warning that the health of the patient is likely to be deteriorating.

In a typical implementation, when the sensor unit 11 determines that the patient is receiving gas from the respiratory device (i.e. when the sensor unit 11 detects a variation in the flow/pressure of gas in the pipe), the sensor unit 11 will implement periodic sampling of the flow rate/pressure, in which the flow rate/pressure is monitored for the duration of a sampling phase/period with the sampling phase recurring at predefined intervals. For example, this periodic sampling could involve, whilst the sensor unit 11 detects a variation in the flow/pressure of the gas in the pipe, monitoring of the flow rate/pressure for the duration of a 30 second sampling phase with each sampling phase being separated by a 20 minute interval. In this case, if the patient were to stop receiving gas from the respiratory device during the interval between sampling phases, then the sensor unit 11 would not implement a sampling phase at the end of the interval, but would initiate a further sampling phase when it determines that the patient has again started to receive gas from the respiratory device.

In addition, when monitoring the flow rate/pressure, the sensor unit 11 can be configured to take discrete measurements at a predefined sample rate. For example, if the sensor unit 11 were to implement periodic sampling, with a sampling phase duration of 30 seconds, the sensor unit 11 could be configured to take measurements at a sample rate of 100 ms, such that 3000 measurements are taken during each sampling phase.

In embodiments in which the processor 122 determines a measure of the respiratory rate by calculating the separation between peaks in the monitored flow rate/pressure, the processor 122 can be configured to implement a noise elimination process to eliminate any variations in the monitored flow rate/pressure that are not caused by respiration of the patient, and that would otherwise cause the frequency determined by the peak detection process to be an inaccurate indication of the respiratory rate. To do so, the processor could be configured to use one or both of a threshold peak width and a threshold peak amplitude to exclude peaks that are too short/narrow and/or too small to have been caused by the respiration of the patient.

In addition, as it is intended that it should be possible to use this detection process with patients receiving domiciliary respiratory therapy, the detection process should be capable of accurately detecting the deterioration in the health of a patient even when the patient is not in a controlled environment (e.g. they could be walking, talking, coughing, etc.). In particular, when not in a controlled environment the behaviour of the patient could induce variations in the respiratory rate that are not part of a longer term trend. To account for such short term variability, the processor 122 could be configured to calculate a median value for the respiratory rate. These median values would then be used when implementing the trend analysis. By way of example, in a particular embodiment, the sensor unit 11 could be configured to implement periodic sampling and to take discrete measurements at a predefined sample rate during each sampling phase. The processor 122 could then determine a measure of the respiratory rate for that sampling phase by calculating the separation between any detected peaks and then determining the median value for the separation between the detected peaks.

Furthermore, to account for variations in the respiratory rate that occur due to the daily habits of a patient, the processor 122 could be configured with a plurality of daily time slots, and to implement the trend analysis at the end of each time slot using the respiratory rate data captured during the most recent/latest time slot and the corresponding time slots of preceding days. For example, when a patient is sleeping their respiratory rate is significantly slower than when the patient is awake and doing physical activity. Consequently, the processor 122 could be configured to separate each day into three time slots, 08:00 to 16:00 (day), 16:00 to 00:00 (evening), and 00:00 to 08:00 (night). The processor 122 could then be configured to implement the trend analysis at the end of each time slot, (day, evening and night) using the respiratory rate data captured during that time slot and the corresponding time slot on each of a predefined number of preceding days, such that the trend analysis is implemented three times each day.

The processor 122 could be configured to implement a trend analysis that comprises calculating a C statistic (i.e. Young's C statistic for time series analysis) for the measured respiratory rate. In this regard, time series analysis with the C statistic identifies whether a trend, defined as any systematic departure from random variation, is evident in a series of data points. The formula to calculate the C statistic is:

$$C = 1 - \frac{\sum_{i=1}^{n-1}(X_i - X_{i+1})^2}{2 \cdot \sum_{i=1}^{n}(X_i - M_x)^2}$$

Wherein $X_i$ is the points in the data series and $M_x$ is the average of the X values.

Depending upon the value of C, there are three different conditions:
1) $0 < C \leq$ threshold means that there is weak trend in the data series;
2) Threshold $< C \leq 1$ means that there is an strong trend in the data series;
3) And if $C \leq 0$ or $C > 1$ means there is not a trend in the data series.

The threshold used to determine whether there is a strong trend in the data series is configurable, and would at least initially be calibrated using test data. The configuration/calibration of the threshold could then be refined through use. In particular, usage data could indicate that the threshold value should be varied at different times of the year (e.g. to account for seasonal changes) and/or to take account of changes in environmental conditions such as temperature, humidity etc. However, the C statistic merely determines if there is a trend, and does not indicate whether that trend is upward or downward. Therefore, if the calculated value of C indicates that there is a trend, then the trend analysis implemented by the processor 122 further comprises a comparison of the measured respiratory rate with a reference/representative/characteristic respiratory rate to determine if there is an upward trend. Preferably the reference/representative/characteristic respiratory rate is patient-specific, and dynamically calibrated.

In this regard, when implementing the trend analysis the processor makes use of the respiratory rate data that has been captured over a predefined period, referred to herein as the analysis period. Therefore, in order to determine a characteristic respiratory rate, the processor can be configured to calculate an average of the respiratory rate data that was captured prior to the analysis period. For example, the processor may be configured to implement the trend analysis using the respiratory rate data captured during an analysis period that covers the last m days. Then, if the apparatus has been in use for a total of m+n days, the characteristic respiratory rate will be calculated using the respiratory rate data that was captured during a reference period that covers $day_1$ to $day_n$ (i.e. the days that preceded the analysis period). In doing so, the characteristic respiratory rate calculated by the processor would be continually updated as more respiratory rate data becomes available thereby compensating for any changes in the state of the patient over time. For example, if the patient's condition were to improve over the first few days/weeks of receiving respiratory therapy, such that the patient's respiratory rate were to generally decrease over that period, then reference respiratory rate will also decrease. Consequently, the trend analysis will make use of this decreased reference respiratory rate to determine if there has been a subsequent upward trend in the patient's respiratory rate.

The comparison of the monitored respiratory rate with a reference respiratory rate to determine if there is an upward trend could comprise calculating a value that is indicative of whether the trend in the respiratory rate data captured over the analysis period is an upward trend. By way of example, this representative value (Inc) could be calculated using the following formula:

$$Inc = (X_n - \text{baseline}) \cdot \sum_{i=1}^{n-1} (X_{i+1} - X_i)$$

Wherein Xi is the points in the data series and n is the length of the reference period in days. If Inc is greater than 0, then the trend in the data is upward, and the value for the C statistic can then be compared with the predefined threshold to determine if a warning should be generated.

Unlike systems that monitor sound and/or motion to determine breathing patterns, the apparatus described herein can be provided as part of or as an accessory or peripheral to a respiratory device that is provided to a patient. The apparatus is therefore much less intrusive, more straightforward to setup, and requires less overall equipment, which is particularly important when intended for use in domiciliary environments. In addition, by monitoring a patient during the use of a respiratory device, the methods and apparatus described herein provide for greater accuracy in the measurement of the patients respiratory rate, as the patients respiration is sensed directly rather than indirectly. Moreover, the methods and apparatus described herein are not limited to the monitoring of the patient whilst asleep.

In addition, conventional methods of using breathing related measurements for predicting the onset of a medical episode that rely on comparing a monitored pattern of breathing with a comparable baseline pattern are significantly more complex than the methods described herein. In particular, to implement these conventional methods it is necessary to detect the breathing of the subject, ascertain the type of breathing pattern being displayed by the subject, and compare the breathing pattern with a baseline pattern of the same type. Each of these steps introduces potential inaccuracies that impact on the effectiveness of the prediction.

It will be appreciated that individual items described above may be used on their own or in combination with other items shown in the drawings or described in the description and that items mentioned in the same passage as each other or the same drawing as each other need not be used in combination with each other. In addition, the expression "means" may be replaced by actuator, system, unit or device as may be desirable. In addition, any reference to "comprising" or "consisting" is not intended to be limiting in any way whatsoever and the reader should interpret the description and claims accordingly.

Furthermore, although the invention has been described in terms of preferred embodiments as set forth above, it should be understood that these embodiments are illustrative only. Those skilled in the art will be able to make modifications and alternatives in view of the disclosure which are contemplated as falling within the scope of the appended claims. By way of example, in the above described embodiments the only significant source of variation in the flow/pressure of the gas in the pipe occurs due to the respiration (i.e. inhaling and exhaling) of the patient, wherein inhalation by the patient will increase the flow rate/pressure and exhalation will decrease the flow rate/pressure. However, in an alternative embodiment the respiratory device could be provided with a demand value that automatically controls the supply of gas by opening to provide flow when the user/patient inhales and closing to shut off the supply when inhalation stops. In this alternative embodiment, the only significant source of variation in the flow/pressure of the gas in the pipe will still occur due to the respiration of the patient, as the demand value will automatically open when it detects the inspiration of the user/patient, thereby increasing the flow rate/pressure by allowing the respiratory device to supply gas into the pipe, and automatically close when inspiration has stopped, thereby reducing the flow rate/pressure in the pipe.

The invention claimed is:

1. An apparatus for detecting the deteriorating health of a patient receiving gas from a respiratory device, the apparatus comprising:
a sensor unit that monitors a flow rate or pressure of a gas that is flowing in a pipe that connects the respiratory device to a gas delivery device worn by the patient; and a processor configured to measure a respiratory rate of the patient based on variations in the flow rate or pressure of the gas in the pipe and to implement a trend analysis of the measured respiratory rate;
wherein the sensor unit comprises a sensor device that monitors the variations in the flow rate or pressure that are induced by the respiration of the patient, and to output a signal that is proportional to a derivative of the flow rate or pressure with respect to time;
wherein the sensor device comprises a differential pressure sensor having first and second pneumatic input ports, the first pneumatic input port receives a flow of gas from a first point in the pipe and the second pneumatic input port receives a flow of gas from a second point in the pipe, wherein the second pneumatic input port includes a delay device that delays the flow of gas that flows from the pipe to the differential pressure sensor, such that the differential pressure sensor measures the variation in the pressure of the gas within the pipe and outputs a signal that is proportional to the derivative of the flow rate or pressure with respect to time;

the processor is configured to detect peaks in the monitored flow rate or pressure by implementing discrete-time integration of the output of the sensor device and determines a measure of the respiratory rate of the patient using the separation between the detected peaks, to determine the flow rate or pressure of a flow that is induced by the respiration of the patient, and to then process the determined flow rate or pressure to detect local maxima;

wherein the processor is configured to generate a warning, that indicates that health of the patient is likely to be deteriorating, when the processor determines that there is an upward trend in the measured respiratory rate, determined by the processor using the separation between said detected peaks in the monitored flow rate or pressure and that a magnitude of the trend exceeds a threshold.

2. The apparatus of claim 1, wherein the delay device of the second pneumatic input port comprises a porous material within a hollow center of the second pneumatic input port that acts to delay the flow of gas from the pipe to the differential pressure sensor.

3. The apparatus of claim 1, wherein the delay device comprises at least a portion of the second pneumatic input port is formed from a resilient material that acts to delay the flow of gas from the pipe to the differential pressure sensor.

4. The apparatus of claim 1, wherein the processor is configured to use one or both of a threshold peak width and a threshold peak amplitude to exclude noise when measuring the respiratory rate of the patient.

5. The apparatus of claim 1, wherein the sensor unit is configured to implement sampling phases at predefined intervals when variations in the flow rate or pressure are detected, and the flow rate or pressure is monitored for the duration of each sampling phase.

6. The apparatus of claim 5, wherein the processor is configured to calculate a median value for the separation between the peaks detected during each sampling phase and to use the median value as a measure of the respiratory rate of the patient.

7. The apparatus of claim 1, wherein the processor is configured to implement the trend analysis at the end of each of a plurality of daily time slots using the respiratory rate measured during the latest time slot and corresponding time slots of preceding days.

8. The apparatus of claim 1, wherein the processor is configured to implement a trend analysis that comprises calculating a C-statistic for the measured respiratory rate.

9. The apparatus of claim 8, wherein the processor is configured to generate a warning when the calculated C-statistic indicates a trend and a comparison of the measured respiratory rate with a characteristic respiratory rate indicates an upward trend.

10. The apparatus of claim 1, wherein the processor is configured to determine a characteristic respiratory rate by averaging the respiratory rate measured over a reference period of at least a predefined number of days.

11. The apparatus of claim 1, wherein the processor is configured to implement the trend analysis using the respiratory rate measured over an analysis period of a predefined number of days.

12. The apparatus of claim 1, wherein the processor is configured to determine a characteristic respiratory rate by averaging the respiratory rate measured over the days preceding the analysis period.

13. The apparatus of claim 1, further comprising a transceiver configured to communicate with a remote computer device.

14. The apparatus of claim 13, wherein the processor is configured to cause a communication to be sent using the transceiver that warns the remote compute device that the patient's health is likely to be deteriorating.

15. The apparatus of claim 1, wherein the apparatus uses a respiratory device that is an oxygen supply device and is configured to monitor a flow rate or pressure of oxygen provided by the oxygen supply device.

16. The apparatus of claim 1, wherein the apparatus uses a respiratory device that is a ventilator and is configured to monitor a flow rate or pressure of air provided by the ventilator.

17. The apparatus of claim 1, wherein the apparatus is configured to use a domiciliary respiratory device.

18. A method of detecting exacerbation of a medical condition of a patient receiving gas from a respiratory device, the method comprising:

using a sensor unit configured to monitor a flow rate or pressure of a gas that is flowing in a pipe that connects the respiratory device to a gas delivery device worn by the patient;

using a processor configured to measure a respiratory rate of the patient based on variations in the flow rate or pressure of the gas in the pipe; and using the processor configured to implement a trend analysis of the measured respiratory rate;

wherein the step of using the sensor unit to monitor the flow rate or pressure of the gas that is flowing in the pipe that connects the respiratory device to the gas delivery device worn by the patient comprises using a sensor device of the sensor unit to monitor the variations in the flow rate or pressure that are induced by the respiration of the patient and to output a signal that is proportional to a derivative of the flow rate or pressure with respect to time;

the step of using the processor configured to measure the respiratory rate of the patient based on variations in the flow rate or pressure of gas in the pipe comprises detecting peaks in the monitored flow rate or pressure by implementing discrete-time integration of the output of the sensor device, and determining a measure of the respiratory rate of the patient using the separation between the detected peaks to determine the flow rate or pressure of a flow that is induced by the respiration of the patient, and then processing the determined flow rate or pressure to detect local maxima;

wherein the step of outputting a signal that is proportional to a derivative of the flow rate or pressure with respect to time comprises a differential pressure sensor receiving gas from a first point in the pipe at a first input port and receiving gas from a second point in the pipe at a second input port that acts to delay the flow of gas that flows from the pipe to the second input port of the differential pressure sensor using a delay device; and using the processor configured to determine that there is an upward trend in the measured respiratory rate, based on detecting said peaks in the monitored flow rate or pressure in said pipe and determining the measured respiratory rate of the patient using the separation between said detected peaks, to generate a warning, that indicates that health of the patient is likely to be deteriorating when a magnitude of the trend exceeds a threshold.

19. The method of claim 18, wherein the step of detecting peaks in the monitored flow rate or pressure comprises using one or both of a threshold peak width and a threshold peak amplitude to exclude noise when measuring the respiratory rate of the patient.

20. The method of claim 18, comprising implementing sampling phases at predefined intervals when variations in the flow rate or pressure are detected, and monitoring the flow rate or pressure for the duration of each sampling phase.

21. The method of claim 20, wherein a median value for the separation between the peaks detected during each sampling phase is calculated, and the median value is used as a measure of the respiratory rate of the patient.

22. The method of claim 18, wherein the step of using the processor to implement a trend analysis of the measured respiratory rate comprises implementing the trend analysis at the end of each of a plurality of daily time slots using the respiratory rate measured during the latest time slot and corresponding time slots of preceding days.

23. The method of claim 18, wherein the step of using the processor to implement a trend analysis of the measured respiratory rate comprises calculating a C-statistic for the measured respiratory rate.

24. The method of claim 18, wherein a warning is generated when a calculated C-statistic indicates a trend and a comparison of the measured respiratory rate with a characteristic respiratory rate indicates an upward trend.

25. The method of claim 24, further comprising determining the characteristic respiratory rate by averaging the respiratory rate measured over a reference period of at least a predefined number of days.

26. The method of claim 18, wherein the step of using the processor to implement a trend analysis of the measured respiratory rate comprises using the respiratory rate measured over an analysis period of a predefined number of days.

27. The method of claim 26, comprising determining the characteristic respiratory rate by averaging the respiratory rate measured over a reference period of at least a predefined number of days and wherein the step of determining the characteristic respiratory rate comprises averaging the respiratory rate measured over the days preceding the analysis period.

\* \* \* \* \*